United States Patent [19]

Wall et al.

[11] 4,254,289

[45] Mar. 3, 1981

[54] PROCESS FOR THE PRODUCTION OF ALKENE-1,5-DIOLS

[75] Inventors: Robert G. Wall, Pinole; Shigeto Suzuki, San Francisco; John B. Wilkes, Richmond, all of Calif.

[73] Assignee: Chevron Research Company, San Francisco, Calif.

[21] Appl. No.: 758,727

[22] Filed: Jan. 12, 1977

Related U.S. Application Data

[63] Continuation-in-part of Ser. No. 616,794, Sep. 25, 1975, abandoned, which is a continuation of Ser. No. 458,625, Apr. 8, 1974, abandoned, which is a continuation-in-part of Ser. No. 379,511, Jul. 16, 1973, abandoned.

[51] Int. Cl.³ .......................................... C07C 33/035
[52] U.S. Cl. .................................................... 568/857
[58] Field of Search .................... 260/635 R; 568/857

[56] References Cited

U.S. PATENT DOCUMENTS

| 2,868,846 | 1/1959 | Lawlor et al. ..................... 260/640 |
| 3,574,773 | 4/1971 | Mueller et al. ................. 260/638 R |
| 3,692,848 | 9/1972 | Mueller et al. ................. 260/635 R |

*Primary Examiner*—Joseph E. Evans
*Attorney, Agent, or Firm*—D. A. Newell; J. Stoner, Jr.; W. Keith Turner

[57] ABSTRACT

In the reaction of 3-methyl-3-buten-1-ol with aqueous formaldehyde forming isomeric alkene-1,5-diols, particularly 3-methylene-1,5-pentanediol and 3-methyl-2-pentene-1,5-diol, it has been found that yields of the diols surprisingly are substantially increased if the reaction is effected in the presence of added isobutene and the mol ratio of 3-methyl-3-buten-1-ol to formaldehyde is at least 1:1.

10 Claims, 2 Drawing Figures

PROCESS FOR THE PRODUCTION OF ALKENE-1,5-DIOLS

CROSS REFERENCE TO RELATED APPLICATIONS

This application is a continuation-in-part of U.S. application Ser. No. 616,794, filed Sept. 25, 1975, now abandoned, which, in turn, is a continuation of U.S. application Ser. No. 458,625, filed Apr. 8, 1974, now abandoned, which, in turn, is a continuation-in-part of Ser. No. 379,511, filed July 16, 1973, now abandoned.

BACKGROUND OF THE INVENTION

1. Field of the Invention

This invention relates to a process for the production of alkene-1,5-diols. More particularly, it relates to a process for the production of a mixture of 3-methylene-1,5-pentanediol and the two geometric 3-methyl-2-pentene-1,5-diol isomers from the reaction of isobutene, formaldehyde and 3-methyl-3-buten-1-ol. 3-methylene-1,5-pentanediol has many uses in organic synthesis, and is particularly useful as a precursor for the production of citric acid, as taught in Belgian Pat. Nos. 784,238 and 792,076. Also, the alkenediols can readily be hydrogenated to alkanediols, which are useful in the production of polymers, resins, plasticizers and synthetic lubricants, and as chemical intermediates in the production of materials such as 3-methylvalerolactone.

2. Description of the Prior Art

It is known that an alkenol can be reacted with aqueous formaldehyde in the presence of a base to produce alkenediols. More particularly, U.S. Pat. No. 3,692,848 teaches the reaction of 3-methyl-3-buten-1-ol with aqueous formaldehyde at 235° C. to 400° C., thereby forming 3-methyl-2-pentene-1,5-diol.

Also, U.S. Pat. No. 2,798,996 discloses the reaction of anhydrous paraformaldehyde with mono-ol such as 3-methyl-3-buten-1-ol to produce the diol 3-methylene-1,5-pentanediol.

It is also known that alk-3-en-1-ols can be produced by the reaction of isobutene with aqueous formaldehyde. More particularly, U.S. Pat. No. 3,574,773 teaches the reaction of aqueous formaldehyde with isobutene in the presence of a base, forming 3-methyl-3-buten-1-ol.

Also, U.S. Pat. No. 2,335,027 discloses the reaction of diisobutene with paraformaldehyde to obtain a mono-ol, namely diisobutene carbinol.

SUMMARY OF THE INVENTION

It has been found that the process for the production of alkene-1,5-diols comprising:

(1) contacting in a reaction zone a reaction mixture comprising 3-methyl-3-buten-1-ol and aqueous formaldehyde;

(2) reacting said mixture at an elevated temperature and pressure for a period of time sufficient to form said alkenediols, said temperature being below the critical temperature of said reaction mixture, can be improved by effecting the reaction in the presence of added isobutene at a 3-methyl-3-buten-1-ol to formaldehyde mol ratio of at least 1:1.

When sufficient isobutene and formaldehyde are added to the reaction mixture, the process of the invention permits the production of alkenediols with no net consumption of 3-methyl-3-buten-1-ol, so that the overall result is production of alkene-1,5-diols from isobutene and aqueous formaldehyde in a single-stage reaction.

The exact reasons as to why the process of the present invention is successful in producing the diols in a one-step reaction are not easily pinpointed, although reaction conditions as described herein have been found to give very good yields of the diols. We have noted that added isobutene substantially increases the yield of the diols (i.e., 3-methylene-1,5-pentanediol and 3-methyl-2-pentene-1,5-diol), whereas other olefins in similar systems do not appear to have similar effects. E.g., added isopentene (2-methyl-2-butene) when making the mono-ol 2,3-dimethylbutene-1-ol and the corresponding diols does not appear to have the same effect as does the added isobutene in making the diols in the process of the present invention.

In the process of the present invention, the effluent withdrawn from the reaction zone, exclusive of isobutene, contains an appreciable amount of the diols, usually at least 2 weight percent of the diols, and preferably at least 4 weight percent of the diols. Typically the reaction zone is operated at conditions sufficient to form between about 4 and 40, more usually between about 6 and 20, weight percent of the diols in the effluent withdrawn from the reaction zone, exclusive of isobutene. The isobutene is excluded from the effluent for purposes of calculating the weight percent diols for convenience, as the isobutene usually readily flashes off from the effluent mixture. Conditions that our data indicate are preferable for achieving relatively high yields of the diols in the effluent include the presence of added isobutene as a centrally important factor; the use of temperatures below the critical temperature of the reaction mixture, preferably a temperature between 150° and 300° C., and more preferably between about 180°–250° C.; the maintenance of a pH in the reaction zone between about 4 and 7, preferably by the addition, periodically or continuously, of a buffer comprising a weak polybasic acid and the salt of a weak polybasic acid; and the use of aqueous reaction conditions, preferably including the use of aqueous formaldehyde.

DETAILED DESCRIPTION OF THE INVENTION

Figure 1:
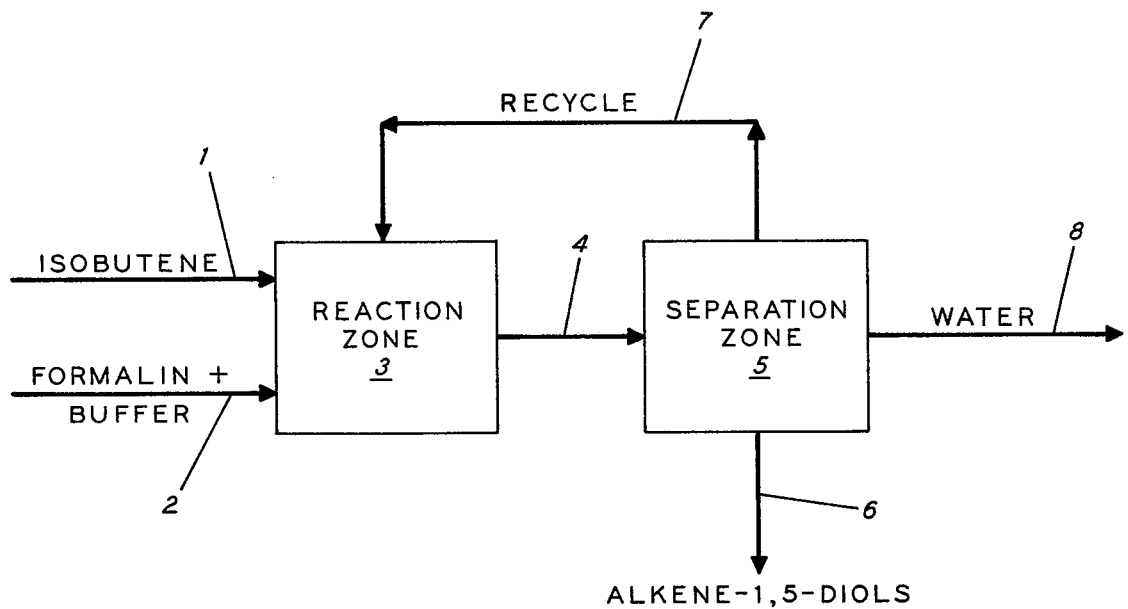
FIG. 1 is a simplified schematic flow diagram of a preferred embodiment of the invention, in which the desired alkenediols are produced on a continuous basis.

One mol of isobutene can be reacted with one mol of formaldehyde according to the following equation:

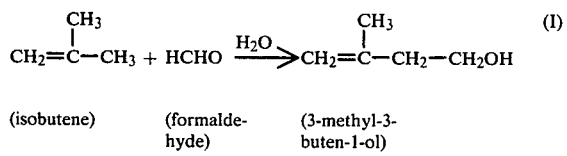

```
         CH3                          CH3            (I)
         |                            |
CH2=C—CH3 + HCHO   ─H2O→   CH2=C—CH2—CH2OH (isobutene)    (formalde-      (3-methyl-3-
                hyde)          buten-1-ol)
```

A second mol of formaldehyde can be added to the product of (I) to form isomeric diadducts of isobutene, according to the following equation:

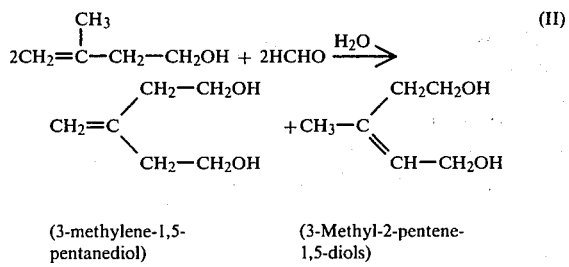

(3-methylene-1,5-pentanediol)   (3-Methyl-2-pentene-1,5-diols)

Surprisingly when reaction (II) is carried out in the presence of added isobutene, and the mol ratio of monool to formaldehyde is at least 1:1, greatly increased yields of the diols result. Viewed another way, when the two reactions (I and II) are carried out concurrently, yields of the diols are surprisingly higher than if the two reactions were carried out separately. The concurrent reaction of this invention may be represented as follows:

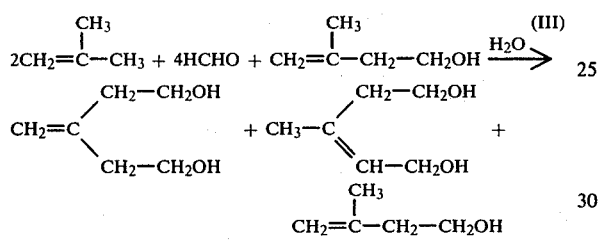

By higher yields of the diols, it is meant that the mols of diols from the concurrent reactions, based on converted 3-methyl-3-buten-1-ol, isobutene, or formaldehyde, are higher than would be obtained if the reactions were carried out sequentially, as illustrated by equations (I) and (II).

Carrying out the reactions concurrently has many other process advantages besides the higher yields of diols. One advantage is the use of 3-methyl-3-buten-1-ol as a solvent to dissolve isobutene, thus facilitating liquid-phase conditions essential in reaction (I). Starting with a mixture containing 3-methyl-3-buten-1-ol allows the 3-methyl-3-buten-1-ol to act both as a reactant and as a solvent for the isobutene. The 3-methyl-3-buten-1-ol is also a solvent for the aqueous formaldehyde, further facilitating liquid-phase contacting of the reactants.

Another important advantage is that the process of the invention allows one to form the desired diols from isobutene and formaldehyde in a single-stage, continuous process in which make-up isobutene and aqueous formaldehyde are fed to a reactor. Crude product from the reactor is separated into various portions, for example an alkenediol product portion and a second portion comprising water, formaldehyde, 3-methyl-3-buten-1-ol and isobutene, which, after partial dehydration, is recycled to the reactor.

The process of this invention is carried out at a temperature from 150° C. to 300° C., with 180° to 250° C. being preferred. It is important, however, that the reaction be carried out with at least part of the reactants in the liquid phase. Thus, the reaction temperature should not exceed the critical temperature of the reaction mixture. The critical temperature will depend upon the concentration and physical properties of reactants and any solvents present in the reaction mixture. The critical temperature of any mixture can readily be estimated from Kay's rule, R. C. Reid and T. K. Sherwood, "The Properties of Gases and Liquids", 2d Ed., 1966, using the known physical properties of the pure components of the mixture. A critical temperature of 132° C. was estimated for formaldehyde by comparison with acetaldehyde and from the differences in critical temperatures for various alcohols.

Reaction pressure is not a critical variable, and may vary widely within the scope of the invention. The pressure should be high enough to keep most of the materials in the liquid phase at the reaction temperature. In particular, it should be high enough to keep a substantial fraction of the added isobutene dissolved in the liquid phase. Preferably at least about 5% of the liquid phase should be isobutene. Normally the reaction is carried out at pressures from 100 to 5000 psig, with 200 to 2000 psig being preferred. The higher pressures are required for high reaction temperatures, although high pressures may also be used at lower reaction temperatures.

Preferably aqueous formaldehyde is used in the reaction. Formaldehyde is economically available in an aqueous solution (formalin), typically containing 37% formaldehyde and about 52–63 weight percent water. A preferred aqueous formaldehyde is that disclosed in ASTM D-2578-68. Other aqueous solutions of formaldehyde can be used with widely varying amounts of formaldehyde and water. Preferably at least 30 weight percent of the formaldehyde solution is water. It is preferred to use aqueous formaldehyde not only because it is economically available, but also because water has some beneficial effect on the reaction. Commercially available formaldehyde solutions normally contain small amounts of formic acid and from 1 to 10% methanol as a stabilizer. These small amounts of methanol do not have to be removed from the formaldehyde prior to reaction.

Figure 2:
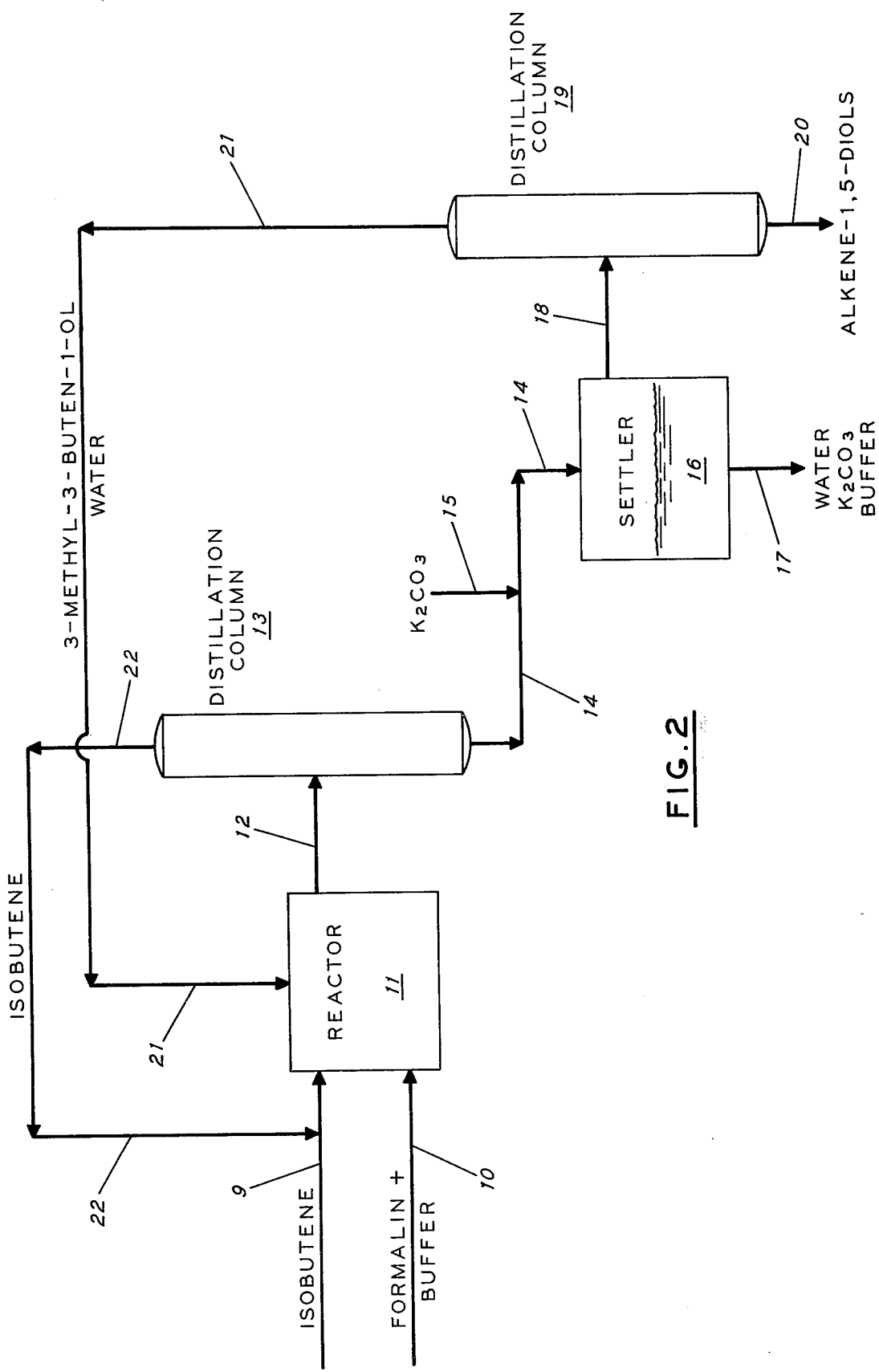
FIG. 2 is a more particular schematic flow diagram of the preferred embodiment of the invention illustrated in FIG. 1.

In the preferred recycle embodiment of the invention, illustrated in FIGS. 1 and 2, anhydrous formaldehyde (paraformaldehyde) is suitable, if water is initially charged to the reactor and not removed from the recycle stream. Because of the high costs of paraformaldehyde, however, it is preferred to start with aqueous formaldehyde and at least partially dehydrate the recycle stream.

In addition to the small amounts of formic acid normally contained in commercially available formaldehyde, small amounts of methanol and formic acid are formed during the reaction by decomposition of formaldehyde, particularly when the pH of the mixture is greater than 7. Formic acid causes formaldehyde solutions to be acidic (pH <4.0), and these acidic conditions lower the yields of the diols. Thus, to minimize the formation and the effect of formic acid on the reaction, it has been found that the pH of the reaction mixture must be maintained from about 4.0 to 7.0, as measured by standard glass and calomel electrodes at ambient temperature and pressure.

Preferably the pH is maintained from 5.0 to 6.0 during the reaction. The pH of the reaction mixture is maintained within the 5.0–6.0 level by the addition of from 0.01 to 5, preferably 0.5 to 1.0, weight percent of suitable buffers based on the aqueous formaldehyde solution. The buffer is made up of a weak acid and the salt of a weak acid. Preferably the buffers are mixtures of polybasic acids and salts of polybasic acids. By weak acids, it is meant those acids which have a pKa larger than 2.8. The buffers may be either inorganic or organic compounds or mixtures thereof. Satisfactory inorganic buffer systems include mixtures of dihydrogen sodium phosphate and disodium hydrogen phosphate, the same mixture of potassium salts, etc. Some organic buffer systems include monopotassium orthophthalate, monosodium citrate, etc. Mixtures of disodium hydrogen phosphate with citric acid or diglycolic acid are the preferred buffers.

Small amounts of ammonia, from 0.2% by weight of the formaldehyde solution to 0.6%, are also effective in maintaining the pH in the desired range. Also, acid-ammonia combinations can be used, for example: $NaH_2PO_4$-$NH_3$, phthalic acid-$NH_3$.

The reaction can be carried out in the presence of various solvents which can be utilized to change the critical temperature of the mixture and increase the solubility of the isobutene in the reaction mixture. Suitable solvents include methanol, ethanol, isopropyl alcohol, isobutanol, dioxane, etc., with the lower alcohols being preferred. Isopropyl alcohol is preferred, if a solvent is used. The amount of water in the reaction mixture can also be varied greatly to change the critical temperature and the solubility of the isobutene.

Reaction time is, of course, dependent upon reaction temperatures, and is varied so as to obtain desired yields of diols. Diol yields are readily determined with a liquid-gas chromatograph. Within the preferred temperature range of 180° to 250° C., a reaction time from 5 to 180, preferably 30 to 90, minutes is preferred.

The formaldehyde reacts with both isobutene and 3-methyl-3-buten-1-ol, as shown in equations (I) and (II). The mol ratio of 3-methyl-3-buten-1-ol to formaldehyde charged may vary widely within the scope of the invention. However, where the mol ratio is at least 1:1, surprisingly improved yields of diol are obtained. Usually a mol ratio of 3-methyl-3-buten-1-ol to formaldehyde in the range 1:1 to 10:1, respectively, is satisfactory. The range 1:1 to 2.5:1 is preferred.

The amount of isobutene added to the reaction mixture can vary widely within the scope of the invention. Even small amounts of from 5 to 10 weight percent isobutene in the reaction solution increases the yield of the diols. The amount of isobutene added must be at least 5 weight percent, based on the total charge. Preferably, however, from 20 to 40 weight percent is isobutene. By "weight percent isobutene" is meant the weight percentage of isobutene relative to the total weight of the aqueous formaldehyde, 3-methyl-3-buten-1-ol and isobutene. Larger quantities of isobutene can also be used.

In the preferred recycle embodiment of the invention, the mol ratio of formaldehyde:(isobutene+3-methyl-3-buten-1-ol) will vary from 0.1–2.0:1.0, with a preferred ratio of 0.2–0.8:1.

The alkenediols are separated from the reaction mixture using conventional distillation techniques. In a continuous distillation the alkenediols and high-boiling by-products are taken off as bottoms, and the isobutene, water, formaldehyde and 3-methyl-3-buten-1-ol and some intermediate products are taken off overhead and recycled to the reactor after partial dehydration.

The water is separated (salted out) by adding a concentrated aqueous potassium carbonate solution (approximately 70% $K_2CO_3$) in a weight about equal to the weight of the water present in the reaction product. When isopropyl alcohol is used as a solvent, the 3-methyl-3-buten-1-ol and isopropyl alcohol are almost insoluble at 22°–26° C. in a solution of equal weights of $K_2CO_3$ and water, and thus the water-$K_2CO_3$ solution can be phase-separated from the alcohols. When methanol is used as a solvent, the methanol must be removed by distillation before salting out the water.

In the recycle embodiment of the invention, other distillations and/or phase separations can be utilized to reduce the quantity of water in the recycle stream or to further purify the crude alkene-1,5-diol product. A bleed stream can be utilized to prevent the buildup of any by-products.

DETAILED DESCRIPTION OF THE DRAWINGS

FIG. 1 is a schematic flow diagram of the preferred recycle embodiment of the invention. In the drawing, isobutene and the formalin-buffer solution are charged to reaction zone 3 via lines 1 and 2, respectively. The reaction product is charged via line 4 to separation zone 5, wherein the desired alkene-1,5-diols are separated from the reaction product and removed via line 6, while the isobutene, formaldehyde and 3-methyl-3-buten-1-ol are separated and recycled to the reaction zone via line 7, and all or a portion of the water is separated and removed via line 8.

In a preferred embodiment, a continuous longitudinal or plug-flow-type reactor rather than a batch-type reactor is utilized. In this preferred embodiment, the product is separated into two or more portions by use of a conventional distillation column.

FIG. 2 is a more particular schematic flow diagram of the preferred recycle embodiment of the invention. In the drawing, isobutene and the formalin-buffer solution are charged to reactor 11 through lines 9 and 10, respectively. The reaction product is charged via line 12 to distillation column 13, where the reaction product is separated into an overhead isobutene fraction, which is recycled via line 22, and a bottoms fraction 14. Aqueous $K_2CO_3$ is added via line 15 to the bottoms fraction, and a phase separation occurs in settler 16. A water-$K_2CO_3$-buffer phase is removed via line 17, and an alcohol-water phase is fed via line 18 to second distillation column 19, wherein an overhead fraction of 3-methyl-3-buten-1-ol and water is recycled via line 21 to reactor 11. The bottoms fraction, which contains the desired alkene-1,5-diols, is discharged via line 20.

The attached figures are but schematic drawings of preferred embodiments, and it is obvious that various modifications of the flow scheme can be made by one skilled in the art.

In this single-stage, preferred embodiment, no make-up 3-methyl-3-buten-1-ol is necessary, as each mol of this alcohol consumed is replaced by another mol formed from the reaction of one mol of isobutene with one mol of formaldehyde.

By carrying out the reactions in this manner, one avoids the added expense of two reactors, in the first of which 3-methyl-3-buten-1-ol is formed according to equation (I) and is then separated from the reaction mixture and reacted with formaldehyde in a second reactor according to equation (II).

EXAMPLES

The following examples will serve to illustrate the invention, but they are not considered to be limiting.

EXAMPLE 1

Reaction of formaldehyde and 3-methyl-3-buten-1-ol in the presence of added isobutene Example 1 illustrates the process of the invention in which increased yields of diols result from the addition of isobutene.

A 3.7-liter autoclave was charged with 720 g (8.36 mols) of 3-methyl-3-buten-1-ol, 700 g of isopropyl alcohol, 205 g of 36.2% formalin, 338 g (6.04 mols) of isobutene, 3.5 g of disodium hydrogen phosphate and 1.3 g of diglycolic acid. The formalin-buffer solution had a pH of 6.1. The autoclave was heated to 215° C. and an additional 415 g of 36.2% formalin solution was pumped into the autoclave over a 25-minute period (total amount of formaldehyde 7.48 mols). The autoclave was stirred and heated at 215° C. for 65 minutes more. During this time, the pressure decreased from an initial value of 2100 to 1600 psig. The reactor was cooled and 136 g of isobutene was bled off. The liquid reaction mixture was distilled to give an additional 99 g of isobutene, for a total recovery of 235 g (4.215 mols) of isobutene. The remainder of the reaction product contained 690 g (8.04 mols) of 3-methyl-3-buten-1-ol and 259 g (2.24 mols) of alkene-1,5-diols. No formaldehyde was recovered. The pH of the final reaction product was 5.4.

The following summary is based on the above data:

3-methyl-3-buten-1-ol reacted to form some undetermined by-product.

However, in the above example, essentially all of the converted isobutene and 3-methyl-3-buten-1-ol are recovered in the product diol, and thus the yield of alkene-1,5-diols based on 3-methyl-3-buten-1-ol or isobutene is essentially 100 mol percent.

EXAMPLE 2

Reaction of formaldehyde and 3-methyl-3-buten-1-ol without added isobutene

Example 2 is a comparative example illustrating the reaction of equation (II) wherein the reaction of 3-methyl-3-buten-1-ol and formaldehyde is carried out in the absence of added isobutene.

The same reactor as Example 1 was charged with 1110 g (12.9 mols) of 3-methyl-3-buten-1-ol, 230 g (2.8 mols) of 36.5% formalin, 700 g of isopropyl alcohol, 3.5 g of disodium hydrogen phosphate and 1.3 g of diglycolic acid. The formalin-buffer solution had a ph of 5.9. This mixture was stirred and heated until a temperature of 215° C. was reached. Then an additional 5.73 mols of 36.5% formalin was pumped in for a total of 8.53 mols of formaldehyde. The mixture was stirred and heated at 215° C. for an additional 65 minutes. During this time, the pressure was in the range 300–500 psig. The reactor was then cooled and the contents were analyzed. The reaction product contained 575 g (6.7

|  |  |  | Converted |  | Diol Yield (Mol %) Based on: | |
|---|---|---|---|---|---|---|
| Component | Charged (Grams) | Recovered (Grams) | (Grams) | (Mols) | Isobutene & 3-Methyl-3-buten-1-ol | Formaldehyde |
| Isobutene | 338 | 235 | 103 | 1.84 | — | — |
| 3-Methyl-3-buten-1-ol | 725 | 690 | 35 | 0.41 | — | — |
| Formaldehyde | 224 | 0 | 224 | 7.48 | — | — |
| Alkene-1,5-Diols | 0 | 259 | — | — | 99.5[1] | 54.2[2] |

[1] Yield = [(mols diols) ÷ (mols isobutene converted + mols of 3-methyl-3-buten-1-ol converted)] × 100 = (2.24 ÷ 2.25)100 = 99.5 mol %.

[2] Yield = [(mols of formaldehyde converted to diol) ÷ (mols formaldehyde converted)] × 100 = [2 × mols isobutene converted + mols 3-methyl-3-buten-1-ol converted) ÷ (mols formaldehyde converted)] × 100 = [(2 × 1.84 + 0.41) ÷ 7.48] × 100 = 54.2 mol %.

In simultaneous reactions, as illustrated in equation (III) and Example 1, yields based on any one of the reactants isobutene, formaldehyde and 3-methyl-3-buten-1-ol can be difficult to determine, because the 3-methyl-3-buten-1-ol is both a reactant and a product. These yields are difficult to determine, because one cannot tell whether: (1) the isobutene reacted with 1 mol of formaldehyde forming 3-methyl-3-buten-1-ol; (2) isobutene reacted with 2 mols of formaldehyde forming the desired alkenediols; (3) the charged 3-methyl-3-buten-1-ol reacted with 1 mol of formaldehyde, forming the desired alkenediols; or (4) the isobutene or charged mols) of 3-methyl-3-buten-1-ol and 356 g (3.07 mols) of alkene-1,5-diols. No formaldehyde was recovered. The following summary is based on the above data:

|  |  |  | Converted |  | Diol Yield (Mol %) Based on: | |
|---|---|---|---|---|---|---|
| Component | Charged (Grams) | Recovered (Grams) | (Grams) | (Mols) | 3-Methyl-3-buten-1-ol | Formaldehyde |
| 3-Methyl-3-Buten-1-ol | 1110 | 575 | 535 | 6.2 | — | — |
| Formaldehyde | 256 | 0 | 256 | 8.53 | — | — |
| Alkene-1,5-Diols | 0 | 356 | — | — | 49.5 | 36 |

A comparison of the results of Examples 1 and 2 shows that the presence of isobutene doubles the molar yield of alkene-1,5-diols from 3-methyl-3-buten-1-ol.

EXAMPLE 3

Reaction of isobutene and formaldehyde without added 3-methyl-3-buten-1-ol

Example 3 is a comparative example illustrating the reaction of formaldehyde and isobutene according to equation (1). The example was performed so that the yields from Examples 2 and 3 could be combined, illustrating the yields obtained in a two-step process according to equations (I) and (II), as compared to the process of the invention as illustrated in equation (III).

The same apparatus as in Example 1 was charged with 500 g of isopropyl alcohol and 789 g (14.1 mols) of isobutene. After a temperature of 210° C. was reached, a solution of 3.5 g of disodium hydrogen phosphate and 1.3 g of diglycolic acid in 620 g (7.5 mols) of 36.2% formalin was pumped in over a 15-minute period. The formalin-buffer solution had a pH of 6.1. This mixture was stirred and heated at 215° C. for an additional 20 minutes. During this time, the pressure was maintained within the range of 1600–2000 psig by the addition of 202 g of isopropyl alcohol. Periodically, small samples were removed and analyzed. There was no change in composition after 60 minutes. The reaction mixture was cooled and bled to give 553 g (9.9 mols) of isobutene. The pH of the final reaction product was 5.25. The remainder of the product contained 316 g (3.7 mols) of 3-methyl-3-buten-1-ol and 62.5 g (0.54 mol) of alkene-1,5-diols. The following summary is based on the above data.

Combining Examples 2 and 3 as a two-step process for the production of alkene-1,5-diols predicts the following results:

Ultimate alkene-1,5-diol yield based on isobutene converted:

Yield = yield of diol (Example 3) + [yield of 3-methyl 3-buten-1-ol (Example 3) × yield of diol based on 3-methyl-3-buten-1-ol (Example 2)] =

$$12 + (88 \times 0.495) = 55.5\% \text{ (mol)}$$

Similarly, the ultimate yield of alkene-1,5-diol based on formaldehyde converted:

$$7 + (49 \times 0.358) = 24.5\% \text{ (mol)}$$

In a cyclic process, as shown in FIGS. 1 and 2, wherein the reactor is continuously charged with isobutene, formaldehyde and recycle 3-methyl-3-buten-1-ol, the yields of alkene-1,5-diols will be as in Example 1, essentially quantitative, based on isobutene.

Other examples were carried out in essentially the same manner as described in Example 1. These examples are given in Table I.

TABLE I

| Ex. No. | Reactor Size (Liters) | CHARGE[1] Solvent (Kind) | Solvent (Grams) | Isobutene (Grams) | HCHO[2] (Grams) | 3-MB[3] (Grams) | CONDITIONS Time (Min.) | Temp. (°C.) | Press. (psig) | PRODUCTS[5] 3-MB[3] (Grams) | AD[4] (Grams) |
|---|---|---|---|---|---|---|---|---|---|---|---|
| 4 | 1 | None | — | 0 | 176 | 370 | 90 | 207 | 270–320 | 205 | 121 |
| 5 | 3.7 | Methanol | 700 | 313 | 620 | 777 | 120 | 215 | 1000–2000 | 672 | 234 |
| 6 | 3.7 | Hexane | 700 | 0 | 700 | 1063 | 90 | 212 | 1350–900 | 631 | 284 |

[1] All examples contained the same charge of buffer as in Example 1, with the pH of the formalinbuffer solution ranging from 5.9 to 6.1.
[2] Formalin of 37% concentration.
[3] 3-Methyl-3-buten-1-ol.
[4] Alkene-1,5-diols.
[5] Final reaction product pH in Examples 4 and 5 was 5.15 and 5.3, respectively.

In the above Examples 1–6, the isobutene was determined by weight of product condensed in a trap cooled in solid $CO_2$ and acetone. Other products were determined by analysis of gas-liquid chromatography, using an internal standard of 2-ethyl-1-hexanol.

EXAMPLE 7

Reaction of 3-methyl-3-buten-1-ol with formaldehyde in the presence of added isobutene A 14-ml-capacity microbomb was charged with 1.8 g (0.02 mol) of 3-methyl-3-buten-1-ol and 1.61 g (0.02 mol) of 37.8% aqueous formaldehyde containing 0.005 g each of disodium hydrogen phosphate and monosodium dihydrogen phosphate. The pH of this solution was 6.9. Then 1.09 g (0.02 mol) of isobutene was charged. The bomb was sealed and heated for 2 hours at 200° C. After cooling, the bomb was opened, the unreacted isobutene was removed and measured, and the liquid reaction mixture was analyzed by vapor-phase chromatography, using n-octanol as an internal standard. The vapor-phase chromatograph indicated the reaction mixture contained, by weight percent: 36% 3-methyl-3-buten-1-ol and 20% alkene-1,5-diol.

| Component | Charged (Grams) | Recovered (Grams) | Converted (Grams) | Converted (Mols) | Yield, Mol %, Based on Isobutene | Yield, Mol %, Based on Formaldehyde |
|---|---|---|---|---|---|---|
| Isobutene | 789 | 553 | 236 | 4.2 | — | — |
| Formaldehyde | 224 | 0 | 224 | 7.5 | — | — |
| 3-Methyl-3-Buten-1-ol | 0 | 316 | — | — | 88 | 49 |
| Alkene-1,5-Diols | 0 | 62.6 | — | — | 12 | 7 |

What is claimed is:

1. A process for the production of 3-methylene-1,5-pentanediol and 3-methyl-2-pentene-1,5-diol, which comprises:
   (a) feeding a reaction mixture comprising 3-methyl-3-buten-1-ol, formaldehyde and isobutene at a mol ratio of 3-methyl-3-buten-1-ol to formaldehyde of at least 1:1 and wherein from 5 to 40% by weight of said mixture is isobutene and therein contacting the 3-methyl-3-buten-1-ol with the formaldehyde at an elevated temperature and pressure while the pH of the reaction mixture is maintained from about 4.0 to 7.0 for a period of time sufficient to form diols, said temperature being below the critical temperature of said reaction mixture, and (b) withdrawing said diols from the reaction zone.

2. A process in accordance with claim 1 wherein the mol ratio of 3-methyl-3-buten-1-ol to formaldehyde is from 1:1 to 10:1.

3. A process in accordance with claim 2 wherein the mol ratio of 3-methyl-3-buten-1-ol is from 1:1 to 2.5:1.

4. A process in accordance with claim 1 wherein the pH of said reaction mixture is maintained from 4.0 to 7.0 by the addition of a buffer comprising a weak polybasic acid and the salt of a weak polybasic acid.

5. A process in accordance with claim 1 wherein said reaction is carried out at a temperature from 180° C. to 250° C. and at a pressure from 200 psig to 2000 psig, and wherein from 20 to 40 weight percent of said mixture is isobutene, and the pH of said reaction mixture is maintained from 5.0 to 6.0.

6. A process for the production of alkene-1,5-diols, comprising:
(a) contacting in a reaction zone a mixture comprising 3-methyl-3-buten-1-ol, aqueous formaldehyde, and isobutene, wherein said isobutene comprises from 5 to 40 weight percent of said mixture and the 3-methyl-3-buten-1-ol to formaldehyde mol ratio is at least 1:1,
(b) reacting said mixture at a temperature from 150° C. to 300° C. and at a pressure from 100 psig to 5000 psig while the pH of the reaction mixture is maintained from about 4.0 to 7.0 for a period of time sufficient to form a reaction product containing said alkene-1,5-diols, said temperature being below the critical temperature of said mixture,
(c) separating from said reaction product a first portion comprising said alkene-1,5-diols and a second portion comprising formaldehyde, water, isobutene, and 3-methyl-3-buten-1-ol, and
(d) recycling said second portion to said reaction zone.

7. A process in accordance with to claim 6 wherein the pH of said reaction mixture is maintained from 5.0 to 6.0 by the addition of a buffer comprising a weak polybasic acid and the salt of a weak polybasic acid.

8. A process in accordance with claim 7 wherein aqueous formaldehyde is fed to said reaction zone and said second portion is partially dehydrated prior to said recycling.

9. A process in accordance with claim 8 wherein said reaction is carried out at a temperature from 180° C. to 250° C. and at a pressure from 200 psig to 2000 psig, and wherein the pH of said reaction mixture is maintained from 5.0 to 6.0, and from 20 to 40 weight percent of said mixture is isobutene.

10. A process for the production of 3-methylene-1,5-pentanediol and 3-methyl-2-pentene-1,5-diol, comprising:
(a) contacting in a reaction zone a mixture comprising 3-methyl-3-buten-1-ol, aqueous formaldehyde, and isobutene, wherein said isobutene comprises from 20 to 40 weight percent of said mixture and the mol ratio of 3-methyl-3-buten-1-ol to formaldehyde is at least 1:1,
(b) reacting said mixture at a temperature from 180° C. to 250° C. and at a pressure from 200 psig to 2000 psig for a period of time sufficient to form a reaction product containing alkene-1,5-diols, said temperature being below the critical temperature of said mixture, and wherein the pH of said reaction mixture is maintained from 5.0 to 6.0 by the addition of a buffer comprising a weak polybasic acid and the salt of a weak polybasic acid,
(c) separating said reaction product into a first portion comprising isobutene and recycling said first portion to said reaction zone,
(d) separating from said reaction product a second portion comprising water,
(e) separating from said reaction product a third portion comprising 3-methyl-3-buten-1-ol and recycling said third portion to said reaction zone, and
(f) separating from said reaction product a fourth portion comprising alkene-1,5-diols.

* * * * *